United States Patent [19]

Stiefel et al.

[11] Patent Number: 4,585,882

[45] Date of Patent: Apr. 29, 1986

[54] SULFIDO(DISULFIDO)BIS(N,N-SUBSTITUTED DITHIOCARBAMATO)W(VI) COMPLEXES

[75] Inventors: Edward I. Stiefel, Bridgewater; Wie-Hin Pan; Thomas R. Halbert, both of Annandale, all of N.J.

[73] Assignee: Exxon Research and Engineering Co., Florham Park, N.J.

[21] Appl. No.: 635,282

[22] Filed: Jul. 27, 1984

[51] Int. Cl.$^4$ .............................................. C07F 11/00
[52] U.S. Cl. ...................................................... 556/38
[58] Field of Search ...................... 260/429 K; 556/38

[56] References Cited

U.S. PATENT DOCUMENTS 3,852,354 12/1974 Usamoto et al. ............ 260/429 K X
4,098,705 7/1978 Sakurai et al. ............. 260/429 K X
4,315,826 2/1982 Schlicht et al. ............. 260/429 R X

OTHER PUBLICATIONS

Chemical Abstracts, 91, 203504u.
Chemical Abstracts, 92, 157026k (1980).
Chemical Abstracts, 93, 60088q (1980).
Chemical Abstracts, 85, 171006r (1976).
Chemical Abstracts, 89, 156700b (1978).
Chemical Abstracts, 85, 201421s (1976).
Chemical Abstracts, 89, 139639w (1978).
Chemical Abstracts, 94, 129874h (1981).
Chemical Abstracts, 87, 126465 (1977).
Chemical Abstracts, 86, 83036r (1977).

*Primary Examiner*—Helen M. S. Sneed
*Attorney, Agent, or Firm*—Edward M. Corcoran

[57] ABSTRACT

This invention relates to sulfido(disulfido)bis(N,N-substituted dithiocarbamato)W(VI) complexes, their preparation and use. More particularly, this invention relates to compounds of the formula $WS(S_2)(S_2CNR_2)_2$ which are mononuclear, seven-coordinate, neutral W(VI) complexes containing only seven sulfur atoms in the Mo coordination sphere. R is hydrogen, an alkyl, aryl, cycloalkyl group or mixture thereof. Preferably all of the R's are the same and are alkyl groups. These compounds are useful as catalysts or catalyst precursors for removing sulfur from sulfur containing hydrocarbons.

12 Claims, No Drawings

SULFIDO(DISULFIDO)BIS(N,N-SUBSTITUTED DITHIOCARBAMATO)W(VI) COMPLEXES

BACKGROUND OF THE INVENTION

1. Field of the Invention

This invention relates to sulfido(disulfido)bis(N,N-substituted dithiocarbamato)W(VI) complexes. More particularly, this invention relates to compounds of the formula $WS(S_2)(S_2CNR_2)_2$ which are mononuclear, seven-coordinate, neutral W(VI) complexes containing only seven sulfur atoms in the W coordination sphere.

2. Background of the Disclosure

Hanewald and Gattow in "Über Chalkogenolate. 97[1], Wolframthioxanthate," Z. Anorg. Allg. Chem., 471, 165-174 (1980) disclose the preparation of eight coordinate, mononuclear W(IV) and W(V) alkyl thioxanthate complexes. The W(IV) complex is cationic and the W(V) is neutral. Other investigators have prepared dinuclear W(IV) and W(V) compounds containing 1,1 dithiolato ligands.

SUMMARY OF THE INVENTION

Sulfido(disulfido)bis(N,N-substituted dithiocarbamato)W(VI) complexes have now been prepared. These are new compositions of matter which are mononuclear, seven-coordinate neutral, W(VI) complexes containing only seven sulfur atoms in the W coordination sphere and have the general formula $WS(S_2)(S_2CNR_2)_2$ wherein R is H, an alkyl group, cycloalkyl group, aryl group or mixture thereof and preferably an alkyl group. These new compositions have the following structure:

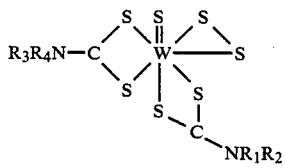

wherein $R_1$, $R_2$, $R_3$ and $R_4$ are the same or different and are H, an alkyl group, aryl group or cycloalkyl group. Preferably $R_1$, $R_2$, $R_3$, $R_4$, $R_5$ and $R_6$ are the same and will be an alkyl group.

These new compounds have been found to be useful catalysts or catalyst precursors for removing sulfur from sulfur containing hydrocarbons and have been prepared by reacting a substituted ammonium tetrathiotungstate with a thiuramdisulfide in non-aqueous media under an inert atmosphere.

DETAILED DESCRIPTION

Sulfido(disulfido)bis(N,N-substituted dithiocarbamato)W(VI) complex compounds of the formula $WS(S_2)(S_2CNR_2)_2$ and of the structure set forth above have now been prepared. These new compounds are mononuclear, seven-coordinate, neutral W(VI) complexes containing seven sulfur atoms bound to the W in the W coordinaion sphere and have been prepared in non-aqueous media by reacting a substituted ammonium tetrathiotungstate with a thiuramdisulfide in non-aqueous media under an inert atmosphere. In the compound two of the sulfur atoms are bound to the W as a disulfide ligand.

These compounds have been found to be useful catalysts or catalyst precursors for removing sulfur from sulfur containing hydrocarbons. When charged into a batch type, stirred reactor containing a mixture of 5% dibenzothiophene in decalin at 350° C. under flowing hydrogen, $WS(S_2)[S_2CN(C_2H_5)_2]_2$ was found to be effective in removing sulfur from the mixture.

The product $WS(S_2)[S_2CN(C_2H_5)_2]_2$ was obtained from a substituted ammonium tetrathiotungstate using N,N,N',N'-tetraethylthiuramdisulfide as an oxidant. This compound is a rare example of a mononuclear W(VI) species containing seven sulfur donor atoms. In this reaction the disulfide group is formed from coordinated sulfur in the $WS_4{}^{2-}$ starting material. The reaction therefore involves a ligand redox process.

As set forth under SUMMARY OF THE INVENTION, the compounds of this invention have the structure:

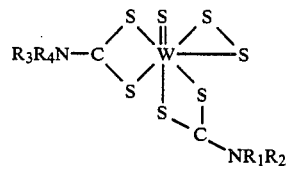

wherein $R_1$, $R_2$, $R_3$ and $R_4$ are the same or different and are H, an alkyl, aryl or cycloalkyl group. Preferably $R_1$, $R_2$, $R_3$ and $R_4$ are the same and are alkyl groups. These compounds are made by reacting one or more suitable tetrathiotungstate salts, $[Cat]_2WS_4$, wherein cat is a monovalent cation, with a thiuramdisulfide in non-aqueous media and in an inert atmosphere. Those skilled in the art know that thiuramdisulfide is the oxidized form of the dithiocarbamato ligand. The nature of the cation Cat effects both the solubility of the tetrathiotungstate salt and the reaction rate, but does not form a part of the neutral complex products of the reaction which are the compounds of this invention. Preferably Cat will be an ammonium or substituted ammonium cation $NH_aR_{4-a}$ wherein a is 0, 1, 2, 3 or 4 and wherein R comprises an alkyl, cycloalkyl or aryl group or mixture thereof. More preferably Cat will be a tetraalkyl ammonium cation, $[NR_4]^+$.

Thiuramdisulfides useful for forming the compounds of this invention have the formula:

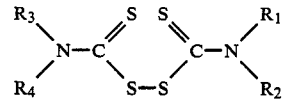

wherein $R_1$, $R_2$, $R_3$ and $R_4$ are the same or different and are H, alkyl, aryl or cycloalkyl groups. Preferably $R_1$, $R_2$, $R_3$ and $R_4$ are the same and are alkyl groups. It should be understood that if the R groups on the thiuramdisulfide are different, then one will obtain an isomeric mixture of the neutral W(VI) complex compounds of this invention.

Green crystals of $WS(S_2)[S_2CN(C_2H_5)_2]_2$ were grown by vapor diffusion of diethylether into a $CHCl_3$ solution of the compound. A crystal was mounted on a diffractometer. Crystal data were obtained on a computer controlled Four Circle Nicolet Autodiffractometer equipped with a graphite-monochromatized MoK ($=0.71073$ Å) radiation source. The crystal was found to be triclinic with space group $P\bar{1}=C_i^2$. Least squares refinement of 15 computer centered reflections ($2\theta > 25°$) at ambient temperature of $20\pm1°$ C. gave the following lattice constants: a=13.143 Å; b=11.192 Å c=10.471 Å; α=98.04°; β=96.54° and γ=111.04°. Its cell volume of 1400 Å$^3$ and Z=2 gave a calculated density of 1.63 g/ml.

Crystal intensity measurements were made and the structure was solved to R=0.038 using standard procedures.

The structural studies of the WS(S$_2$)[S$_2$CN(C$_2$H$_5$)$_2$]$_2$ showed it to be seven-coordinate with four sulfur donor atoms from two dithiocarbamate ligands, two sulfur donors from a disulfide ligand and one sulfur donor from a terminal sulfido ligand. The seven sulfur atoms describe a distorted pentagonal bipyramid around the tungsten. The bond lengths about the W atoms in the coordination sphere of the WS(S$_2$)[S$_2$CN(C$_2$H$_5$)$_2$]$_2$ are set forth in the Table below. The S—S distance of 2.026 Å reveals the presence of the S$_2^{2-}$ ligand in this mononuclear complex.

| Bond* | Length, Å |
| --- | --- |
| W—S (dtc) | 2.454 |
| W—S (dtc) | 2.525 |
| W—S (dtc) | 2.586 |
| W—S (dtc) | 2.505 |
| W—S (disulfide) | 2.365 |
| W—S (disulfide) | 2.400 |
| W—S (sulfide) | 2.137 |
| S—S (disulfide) | 2.026 |

*(dtc) refers to sulfur atoms which are part of dithiocarbamate ligands. (disulfide) refers to sulfur atoms which are part of the S$_2^{2-}$ ligand and (sulfide) refers to the S$^{2-}$ ligand.

The invention will be further understood by reference to the following Examples.

EXAMPLES

Acetonitrile (Burdick & Jackson) was refluxed over CaH$_2$ and distilled before use. Chloroform (Fisher, reagent grade) and ether (MCB, anhydrous) were used as received. N,N,N',N'-tetraethyl thiuramdisulfide (Aldrich) was used as received. (NH$_4$)$_2$WS$_4$ (SPEX) was also used as received. N,N,N',N'-tetraisobutyl thiuramdisulfide was prepared according to Rothstein, et al., "Note Sur La Preparatione des Tetraalkylthiurames," Recueil. Trav. Chim., 73, 561-2 (1975).

Bis(tetraethylammonium)tetrathiotungstate(VI) [N(C$_2$H$_5$)$_4$]$_2$WS$_4$ was prepared using the following method. All operations were carried out under N$_2$ except the work-up which was carried out in air. (NH$_4$)$_2$WS$_4$ (42.5 g) was ground to a fine powder. [N(C$_2$H$_5$)$_4$]OH (25% in methanol, Fluka) (109 ml) was added to 80 ml methanol. This solution was added to the (NH$_4$)$_2$WS$_4$ powder. The resulting mixture was stirred for about 48 h. The yellow precipitate was filtered, washed with methanol, diethylether and air dried. Further drying was carried out under vacuum. The yield was 52 g (75%). The absence of any NH$_4^+$ in the product was confirmed by its infrared spectrum.

In the following examples all operations were conducted under an inert atmosphere such as argon.

EXAMPLE 1

Preparation of (sulfido)(disulfido)bis(N,N-diisobutyl dithiocarbamato)W(VI)

A degassed solution containing 4.088 g (0.010 mol) of tetraisobutylthiuram disulfide in methylene chloride (40 ml) was prepared. To this, 2.86 g (0.005 mol) of bis(tetraethyl ammonium)tetrathioungstate powder was added and allowed to react with stirring, under argon for one hour. The green solution was filtered in air, and the filtrate then collected and concentrated. This crude product was purified by column chromatography (silica gel 60–200 mesh, using 1:1 Hexane-CHCl$_3$ as eluent). The green product thus obtained can be recrystallized from CHCl$_3$ and hexane, and was found to be stable in air once formed.

EXAMPLE 2

Preparation of (sulfido)(disulfido)bis(N,N-diethyldithiocarbamato)W-(VI)

A degassed solution of 2.96 g (0.010 mol) of Tetraethylthiuram disulfide in 50 ml acetonitrile, was added dropwise to a degassed slurry of 2.86 g (0.005 mol) bis(tetraethyl ammonium)tetrathiotungstate in 50 ml acetonitrile. The mixture was stirred under argon for one hour. The dark green solution was filtered in air, the precipitate washed with isopropanol and ether, and dried in vacuo. The product is soluble in acetonitrile, dimethyl formamide, methylene chloride; slightly soluble in ether and toluene, and insoluble in water, pentane and hexane. Once isolated, the green solid is stable in air.

What is claimed is:

1. Mononuclear, seven-coordinate, neutral sulfido(-disulfido)bis(N,N-substituted dithiocarbamato)W(VI) complexes containing only seven sulfur atoms in the W coordination sphere.

2. The complexes of claim 1 having the general formula WS(S$_2$)(R$_2$dtc)$_2$ wherein R is H, an alkyl group, cycloalkyl group, aryl group or mixture thereof.

3. The complexes of claim 2 wherein R consists of alkyl group.

4. Complexes of the structure

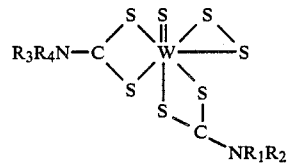

wherein R$_1$, R$_2$, R$_3$ and R$_4$ are the same or different and are H, alkyl group, cycloalkyl group, aryl group or mixture thereof.

5. The complexes of claim 4 wherein R$_1$, R$_2$, R$_3$ and R$_4$ are alkyl.

6. The complexes of claim 5 wherein R$_1$, R$_2$, R$_3$ and R$_4$ are the same.

7. A method of preparing a mononuclear, seven-coordinate, neutral sulfido(disulfido)bis(N,N-substituted dithiocarbamato)W(VI) complex containing only seven sulfur atoms in the W coordination sphere, said process comprising reacting, in a inert atmosphere, a tetrathiotungstate salt of the formula [Cat]$_2$WS$_4$ with a thiuramdisulfide in non-aqueous media for a time sufficient to form said complex.

8. The process of claim 7 wherein Cat is an ammonium or substituted ammonium cation.

9. The process of claim 8 wherein Cat is a tetraalkyl ammonium cation.

10. The process of either of claims 7, 9 or 10 wherein said thiuramdisulfide has the formula

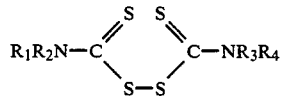
wherein $R_1$, $R_2$, $R_3$ and $R_4$ are the same or different and are H, alkyl, cycloalkyl, and aryl groups or mixture thereof.
11. The process of claim 10 wherein $R_1$, $R_2$, $R_3$ and $R_4$ are the same.
12. The process of claim 11 wherein $R_1$, $R_2$, $R_3$ and $R_4$ are the same and are alkyl.
* * * * *